United States Patent [19]

Papenfuhs et al.

[11] Patent Number: 5,292,967
[45] Date of Patent: Mar. 8, 1994

[54] PROCESS FOR PRODUCING 2,3-DIFLUORO-6-NITROPHENOL

[75] Inventors: Theodor Papenfuhs, Frankfurt am Main; Joachim Hackenbruch, Mainz; Ralf Pfirmann, Karlsruhe, all of Fed. Rep. of Germany

[73] Assignee: Hoechst Aktiengesellschaft, Frankfurt am Main, Fed. Rep. of Germany

[21] Appl. No.: 35,719

[22] PCT Filed: Sep. 25, 1991

[86] PCT No.: PCT/EP91/01829

§ 371 Date: Mar. 23, 1993

§ 102(e) Date: Mar. 23, 1993

[87] PCT Pub. No.: WO92/05141

PCT Pub. Date: Apr. 2, 1992

[30] Foreign Application Priority Data

Sep. 25, 1990 [DE] Fed. Rep. of Germany ....... 4030263

[51] Int. Cl.$^5$ ............................................. C07C 205/20
[52] U.S. Cl. ....................................... 568/709; 568/713
[58] Field of Search ................ 568/709, 713, 704, 706

[56] References Cited

U.S. PATENT DOCUMENTS

| 4,310,711 | 1/1982 | Müller et al. | 568/709 |
| 4,596,893 | 6/1986 | Eifert et al. | 568/709 |
| 5,227,535 | 7/1993 | Pfirmann et al. | 568/709 |

FOREIGN PATENT DOCUMENTS 2614264 10/1977 Fed. Rep. of Germany ...... 568/709

*Primary Examiner*—Werren B. Lone

[57] ABSTRACT

According to a process for producing isomer-free 2,3-difluoro-6-nitrophenol, 2,3,4-trifluoronitrobenzene is reacted with an aqueous solution of alkali metal or alkaline earth metal hydroxide in the absence of organic solvent, at temperatures between about 20° C. and 100° C., the pH value of the reaction mixture is set at about 1 to 6 by acid addition, the resulting product is stream distilled and the 2,3-difluoro-6-nitrophenol is isolated after cooling. No organic solvents are used during any of the steps of the process.

9 Claims, No Drawings

PROCESS FOR PRODUCING 2,3-DIFLUORO-6-NITROPHENOL

SUMMARY OF THE INVENTION

The present invention relates to an improved process for the preparation of 2,3-difluoro-6-nitrophenol in good yields and high selectivity. The compound is a useful precursor for the preparation of quinolonecarboxylic acid antibiotics.

BACKGROUND OF THE INVENTION

It was hitherto only possible to are the compound in question by reaction of sodium hydroxide with 2,3,4-trifluoronitrobenzene at 25° C., subsequent acidification until the product precipitated and filtering off thereof according to the equation

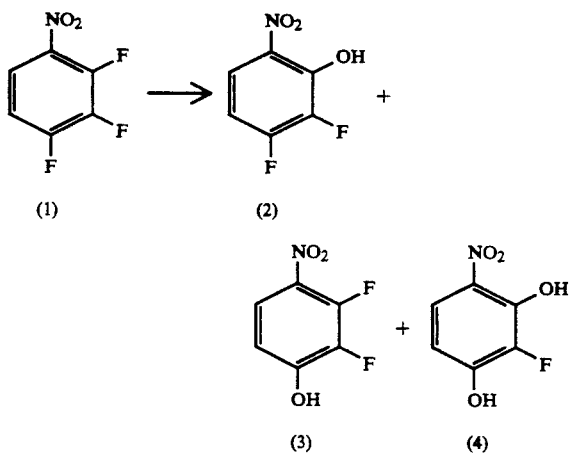

residual isomer contents of 2,3-difluoro-4-nitrophenol (3) occurring.

These isomer contents could be reduced by extraction of the product with non-halohydrocarbons (Ihara Chem. Ind. Co., JP 62/181,241 A2), while in the extraction with halohydrocarbons only a product of about 90 percent purity was obtained.

The addition of polar aprotic solvents proved essential for carrying out the reaction in this method because of the low solubility of 2,3,4-trifluoronitrobenzene (1) and the alkali metal salts of (2) in aqueous alkali metal hydroxide solution (Daiichi Seiyaku Co. Ltd., JP 61/246,150, 246,151, 246,171, 246,188, JP 58/135,840).

The removal of the solvent added (as a rule dimethyl sulfoxide) had to be carried out by extraction from alkaline solution by means of a further organic solvent (chloroform). After acidification of the aqueous phase removed, isolation of the product (2) was likewise carried out by extraction with chloroform (Daiichi Seiyaku Co. Ltd., JP 61/246,150, 1.11.86).

DETAILED DESCRIPTION OF THE PREFERRED EMBODIMENTS OF THE INVENTION

There was therefore a need for a better process in which addition of solubilizers and extraction with organic solvents is unnecessary.

As a solution to the object thus set, it has now been found that isomerically pure 2,3-difluoro-6-nitrophenol can be advantageously prepared in good yields and high selectivity by reacting 2,3,4-trifluoronitrobenzene with aqueous alkali metal hydroxide solution or alkaline earth metal hydroxide solution or suspension, preferably potassium hydroxide solution, in the absence of solvents at temperatures of about 20° C. to about 100° C., preferably of about 30° C. to about 60° C., adjusting the reaction mixture to a pH of about 1 to about 6, preferably of about 2.5 to about 4.5, particularly preferably of about 1.5 to about 3.0, by addition of acid, steam-distilling the resulting product by passing steam into the reaction mixture and isolating the 2,3-difluoro-6-nitrophenol from the distillate after cooling.

It is advantageous to meter the aqueous alkali metal hydroxide solution or alkaline earth metal hydroxide solution or suspension slowly into an initially introduced mixture of water and 2,3,4-trifluoronitrobenzene. A selectivity of 95 to 96% is achieved in this way and the stirrability of the solution is retained.

The isomerically pure 2,3-difluoro-6-nitrophenol is isolated in a yield of 86% of theory by the process according to the invention, no organic solvent being used even in the isolation of the compound mentioned.

Examples of aqueous alkali metal hydroxide solutions which can be used are lithium hydroxide, sodium hydroxide or potassium hydroxide solutions or mixtures thereof, preferably potassium hydroxide solutions, and examples of alkaline earth metal hydroxide solutions or suspensions are calcium hydroxide, strontium hydroxide or barium hydroxide solutions or suspensions or mixtures thereof, preferably calcium hydroxide solutions or suspensions. These solutions are advantageously employed in the form of about 10 to about 80 percent strength solutions or suspensions, preferably of about 30 to about 50 percent strength solutions or suspensions.

Acidification can be carried out using the customary non-oxidizing mineral acids, such as, for example, dilute sulfuric acid, phosphoric acid, hydrochloric acid, hydrobromic acid or hydriodic acid, as well as with sufficiently strong organic acids, such as, for example, formic acid or acetic acid.

The product thus obtained, 2,3-difluoro-6-nitrophenol, can be converted into antibacterial agents by methods known from the literature (Daiichi Seiyaku Co. Ltd., EP 322,815 A2; EP 241,806 A2; JP 62/246,188 A2; EP 206,283 A2; JP 57/203,085; EP 47,005 A1; JP 61/246,171; JP 61/246,151; JP 61/246,172; EP 101,829 A2; JP 58/072,588 A2; Sankyo Co. Ltd., Ube Ind. Ltd., JP 63/0,600,990; JP 62/155,282; JP 61/204,188 A2; Hofmann-LaRoche, F. and Co. A.-G., EP 259,804 A2; EP 216,345 A2; S. Radl, V. Zikan, Collect. Czech. Chem. Commun., 54(2), 506–15 (1989); K. Sakano, S. Yokohama, I. Hayakawa, S. Atarashi, S. Kadoya, Agric. Biol. Chem., 51(5), 1265-1270 (1987); I. Hayakawa, T. Hiramitsu, Y. Tanaka, Chem. Pharm. Bull., 32(12), 4907-13 (1984)).

The process is advantageously carried out at atmospheric pressure; however, it can also be carried out at elevated pressure.

The process according to the invention is illustrated in greater detail by the examples below, without being restricted thereto.

EXAMPLE 1

1.77 kg (10 mol) of 2,3,4-trifluoronitrobenzene are added to 4 l of water. The mixture is then warmed to 40° C. and vigorously stirred. 389.4 g (22 mol) of 31.7% strength potassium hydroxide solution are then added dropwise in such a way that the temperature remains between 40° and 55° C. After about 4 h, the reaction is complete (GC checking). The reaction mixture is brought to pH 3 using 70% strength sulfuric acid at 70° C. Steam is then passed into the solution, the product passing over with it and being isolated after cooling to 10° C. 1.51 kg of 2,3-difluoro-6-nitrophenol having a purity >99.9% (GC) are obtained after drying (melting point 63.5° C.), which corresponds to a yield of 86% of theory.

The mixture can also be acidified with, for example, 85% strength phosphoric acid instead of with the 70% strength sulfuric acid.

EXAMPLE 2

1.77 kg (10 mol) of 2,3,4-trifluoronitrobenzene are added to 2 l of water, and the mixture is warmed to 40° C. and vigorously stirred. 1760 g (22 mol) of 31.7% strength sodium hydroxide solution are then added dropwise in such a way that the temperature does not rise above 60° C. After about 2 h, GC checking no longer shows any starting compound. The reaction mixture is brought to pH 2.5 using 70% strength sulfuric acid. Steam is then passed into the solution, the product passing over with the steam. The separated solution is cooled to 10° C. with stirring and the precipitated solid is filtered off with suction. The water having a residual content of about 0.1% of 2,3-difluoro-6-nitrophenol can be used in a subsequent batch. 1.48 kg of 2,3-difluoro-6-nitrophenol having a purity >99.9% (GC) are obtained after drying (melting point 64° C.), which corresponds to a yield of 85% of theory.

The mixture can also be acidified with, for example, 36% strength aqueous hydrochloric acid instead of with the 70% strength sulfuric acid.

EXAMPLE 3

1.77 g (10 mol) of 2,3,4-trifluoronitrobenzene are added to 2.5 l of water, and the mixture is warmed to 40° C. and vigorously stirred. 1320 g (22 mol) of 40% strength lithium hydroxide solution are then added dropwise in such a way that the temperature rises from 40° to 55° C. within 2.5 h. After this time, GC checking no longer shows any starting compound. The reaction mixture is brought to pH 2 with 70% strength sulfuric acid. It is then worked up, as described in Examples 1 and 2. 1.48 kg of 2,3-difluoro-6-nitrophenol having a purity >99.9% (GC) are obtained after drying (melting point 63.5° C.), which corresponds to a yield of 85% of theory.

The mixture can also be acidified with formic acid instead of with the 70% strength sulfuric acid.

EXAMPLE 4

1.77 kg (10 mol) of 2,3,4-trifluoronitrobenzene and 1.56 kg (21-mol) of calcium hydroxide are heated to 70° C. in 5 l of water and the mixture is well stirred. The reaction is finished after about 6 h, as can be detected by gas chromatography. The mixture is acidified to pH 1.5 with 70% strength sulfuric acid and worked up as described in Examples 1 and 2 (the alkaline solution can also be filtered from inorganic salts at 60° C. before acidification). 1.40 kg of yellow 2,3-difluoro-6-nitrophenol are isolated; a residual content of 2,3-difluoro-4-nitrophenol cannot be detected. The yield corresponds to 80% of theory.

If the mixture is acidified with hydrobromic acid instead of with sulfuric acid, essentially the same result is obtained. Batches using 2.55 kg (21 mol) of strontium hydroxide or 3.68 kg (21.5 mol) of barium hydroxide instead of calcium hydroxide likewise proceed analogously.

We claim:

1. A process for the preparation of isomerically pure 2,3-difluoro-6-nitrophenol, which comprises reacting 2,3,4-trifluoronitrobenzene with aqueous alkali metal hydroxide solution or alkaline earth metal hydroxide solution or suspension in the absence of organic solvent at temperatures of about 20° C. to about 100° C., adjusting the resulting reaction mixture to a pH of about 1 to about 6 by addition of acid, steam-distilling the resulting product and isolating the 2,3-difluoro-6-nitrophenol from the distillate after cooling, no organic solvent being present in any process step.

2. The process as claimed in claim 1, wherein the reaction is carried out at temperatures of about 30° C. to about 60° C.

3. The process as claimed in claim 1, wherein the reaction mixture is adjusted to a pH of about 2.5 to about 4.5.

4. The process as claimed in claim 1, wherein the reaction mixture is adjusted to a pH of about 1.5 to about 3.0.

5. The process as claimed in claim 1, wherein the aqueous alkali metal hydroxide solution employed is aqueous lithium hydroxide, sodium hydroxide or potassium hydroxide solution or mixtures thereof.

6. The process as claimed in claim 1, wherein the aqueous alkaline earth metal hydroxide solution or suspension employed is calcium hydroxide, strontium hydroxide or barium hydroxide solution or suspension or mixtures thereof.

7. The process as claimed in claim 1, wherein said adjusting the reaction mixture to said pH is carried out with a non-oxidizing mineral acid.

8. The process as claimed in claim 1, wherein the process is carried out at atmospheric pressure or elevated pressure.

9. The process as claimed in claim 1, wherein the 2,3,4-trifluoronitrobenzene is first added to a quantity of water which, in combination with the aqueous alkali metal hydroxide solution or alkaline earth metal hydroxide solution or suspension, becomes a non-solvent medium in which the 2,3,4-trifluoronitrobenzene can be stirred together with the dissolved alkali metal hydroxide or dissolved or suspended alkaline earth metal hydroxide.

* * * * *